United States Patent [19]

Beck et al.

[11] 4,197,840
[45] Apr. 15, 1980

[54] PERMANENT MAGNET DEVICE FOR IMPLANTATION

[75] Inventors: Alexander Beck, Forrigel; Jean-Marcel Piffaretti, Rufenacht; Dietmar Weinmann, Nussbaumen, all of Switzerland

[73] Assignee: BBC Brown Boveri & Company, Limited, Baden, Switzerland

[21] Appl. No.: 727,654

[22] Filed: Sep. 29, 1976

[30] Foreign Application Priority Data

Nov. 6, 1975 [CH] Switzerland ............... 14342/75

[51] Int. Cl.² ............................................. A61F 5/01
[52] U.S. Cl. ........................................ 128/76 R; 3/1; 128/1.3
[58] Field of Search ............... 128/1.3, 76.5, 76; 335/303, 302, 306; 148/101; 3/13, 1

[56] References Cited

U.S. PATENT DOCUMENTS

| 3,206,657 | 9/1965 | Moriya | 335/303 |
|---|---|---|---|
| 3,565,073 | 2/1971 | Giesy | 3/1 X |
| 3,752,162 | 8/1973 | Newash | 3/1 X |
| 3,794,041 | 2/1974 | Frei et al. | 128/1.3 X |
| 4,005,699 | 2/1977 | Bucalo | 128/1.3 |

FOREIGN PATENT DOCUMENTS

| 2335475 | 1/1975 | Fed. Rep. of Germany | 128/1.3 |
|---|---|---|---|
| 2363563 | 6/1975 | Fed. Rep. of Germany | 128/283 |
| 2278314 | 2/1976 | France | 3/1 |

OTHER PUBLICATIONS

Jarrett, Journal of Applied Physics, vol. 42, No. 4, pp. 1318–1319 (Mar. 15, 1971).

*Primary Examiner*—Robert W. Michell
*Assistant Examiner*—Michael H. Thaler
*Attorney, Agent, or Firm*—Oblon, Fisher, Spivak, McClelland & Maier

[57] ABSTRACT

A permanent magnet device for implantation in the eyelids including at least two magnet bodies enclosed in substantially shape-dependent manner by an enveloping body consisting of a ductile, tissue-compatible material, the enveloping body being substantially gastight and having at least one constriction in the radial direction.

14 Claims, 7 Drawing Figures

PERMANENT MAGNET DEVICE FOR IMPLANTATION

BACKGROUND OF THE INVENTION

1. Field of the Invention

The present invention relates to a permanent magnet device for implantation, in particular in eyelids.

2. Description of the Prior Art

Eyelids have, as is known, the task of on the one hand protecting the eyes from disturbing environmental influences and on the other hand protecting the eyes themselves from drying. Accordingly, in the event of the inability of an eye to close (lagophthalmos) this task has to be taken over or assisted by artificial means. Analogously, this applies also in the case of the inability to open the eyelids at will (ptosis).

The modern technology of efficient permanent magnets has rendered it possible to implant successfully for this purpose magnets in eyelids. See, for example, W. D. Muhlbauer, H. Segeth, A. Viessmann "Restoration of Lid Function in Facial Palsy With Permanent Magnets", Abstract book of II. Congress of the European Section of International Confederation of Plastic Reconstructive Surgery, Madrid 1973.

Such magnets are constructed in bowed form, selected in pairs for the individual lid curvature from a multiplicity of magnets of various curvature radii and cross-sections and subsequently implanted individually into the upper and lower lid. An adaptation of the magnets, for example, by more bending, involves the danger of breakage of the brittle magnet body. For this reason, the possible adaptation work is restricted to a shortening of the magnet body, for example, by abrasive cutting.

SUMMARY OF THE INVENTION

Accordingly, one object of this invention is to provide a permanent magnet device for implantation, in particular, in eyelids and which can be simply adapted to the individual lid curvature and be anchored securely in the tissue.

Another object of this invention is to provide such a device in which the magnet masses are minimized by use of the (in themselves, not compatible with tissue) high-performance permanent magnets consisting of rare earthscobalt alloys, such as SmCo$_5$.

Briefly, these and other objects of the present invention are achieved by a permanent magnet device in which at least two magnet bodies are enclosed in substantially shape-dependent manner by an enveloping body consisting of a ductile, tissue-compatible material, the enveloping body being substantially gastight and having at least one constriction in the radial direction.

Advantages of this device are the possibility of adaptation of the permanent magnet by bending, and the secure anchorage obtainable in the tissue into which implantation is to be effected.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
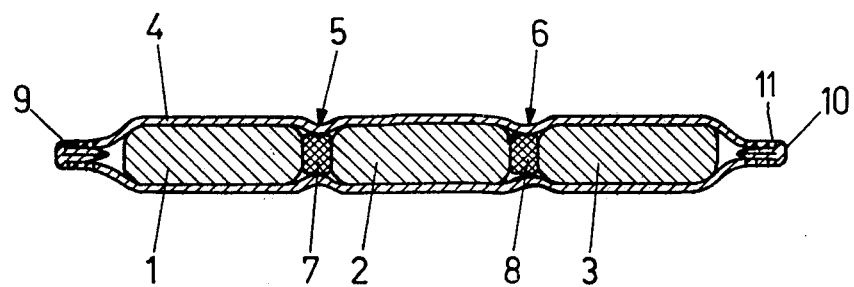
FIG. 1 shows an eyelid permanent magnet device in section, in extended representation.

Referring now to the drawings, wherein like reference numerals designate identical or corresponding parts and more particularly to FIG. 1 thereof, an eyelid permanent magnet device includes three magnet bodies 1, 2, 3. An enveloping body 4 encloses the magnet bodies 1, 2, 3 at least on their longitudinal sides and has, at the ends, the closures 9, 10. Between the individual magnet bodies 1, 2, 3 are spacers 7, 8 which are centered by constrictions 5, 6.

Figure 3:
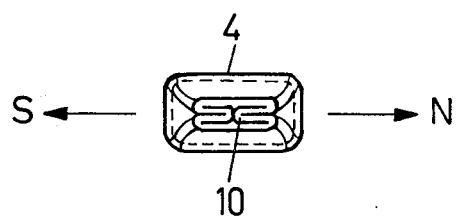
FIG. 3 is the schematic representation of the end closures of the eyelid permanent magnet device of FIG. 1.

The magnetization of the magnet bodies 1, 2, 3 is, in FIG. 1, vertical to the plane of the drawing and in the same sense. In FIG. 3 the magnetization direction is characterized by N=north pole and S=south pole.

The magnet bodies 1, 2, 3 consist of sintered SmCo$_5$ and are fixed in their position by the enveloping body 4. The spacers 7, 8 consist of synthetic rubber material and are accordingly deformable so that the eyelid permanent magnet device can, after the fashion of a polygon, be adjusted to the desired favorable curved form for implantation into the eyelid concerned.

Figure 2:
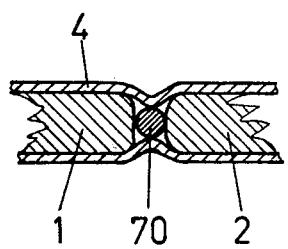
FIG. 2 shows a variant of a built-in spacer between the magnet bodies of the permanent magnet device of FIG. 1.

A round spacer 70 can be seen from FIG. 2. This spacer 70 allows relatively large angles to be adjusted in the polygon and need not necessarily be deformable.

Figure 4:
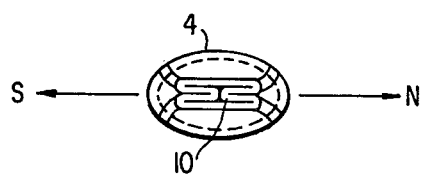
FIG. 4 is an alternate schematic representation of the end closures of the eyelid permanent magnet device of FIG. 1.

The end construction of the closure 10 has been formed according to FIG. 3 by folding. The external shape of the enveloping body is, like that of the enclosed magnet bodies 1, 2, 3, rectangular with rounded edges. The rounding on all sides which is necessary for implanted bodies has been attained at the closures 9, 10 by welding the ends, whereby the desired sealing against tissue fluids entering the permanent magnets or against any gases that may emerge from the permanent magnets is also ensured. Alternatively, the external shape of the enveloping body can be elliptical, as illustrated in FIG. 4.

Figure 5:
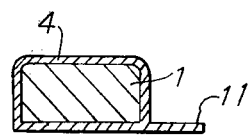
FIG. 5 is an end cross section of the permanent magnet device in a lobe, or rounded projection, shape.
Figure 6:
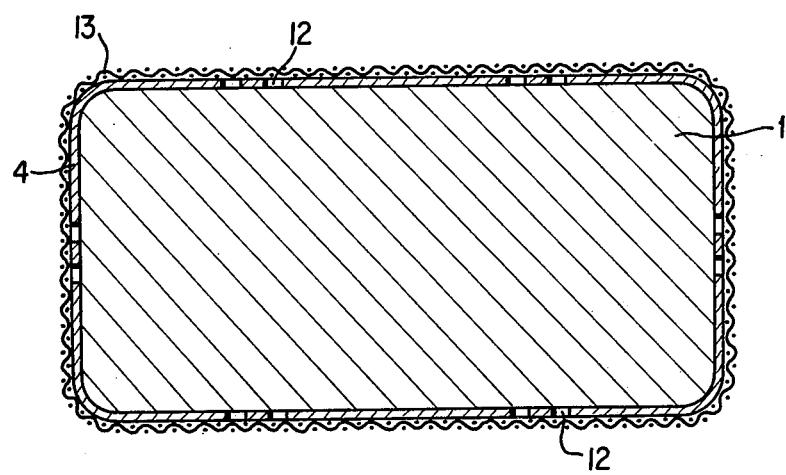
FIG. 6 is an end cross section of the permanent magnet device with the enveloping body constructed partly in net form and covered with a net of tissue compatible material.
Figure 7:
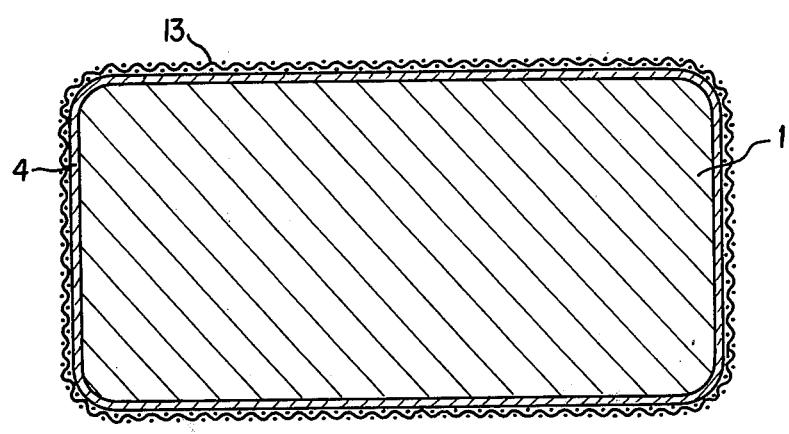
FIG. 7 is an end cross section of the permanent magnet device in which the enveloping body is covered with a net of tissue compatible material.

The enveloping body 4 is produced from gold foil, but could also be produced from other, medically proven metals or plastics. The anchoring in the tissue, which anchoring is necessary because of the high magnetic forces occurring, may be effected by sewing up at the constrictions 5, 6 and at the end-lobe-shaped closures 9, 10. In a preferred embodiment the end lobes are perforated, as in FIG. 1 at 11, for fixing the magnet assembly in the tissue of the living being. Additionally, there could be arranged on the enveloping body 4 a protruberance 11 which renders possible an anchorage in the tissue thereby providing the magnet with a lobe, or rounded projection, shape with respect to the protuberance, as shown in FIGS. 5–7. Also conceivable is a partially netlike construction 12 of the enveloping body 4 and/or a covering of the enveloping body by a net 13 consisting of tissue-compatible material in order that the implanted permanent magnet may at least partially in this anchorage be grown through by tissue. Further similar constructions are likewise conceivably directed to minimizing the surface pressure created by the attraction or repulsion forces of the magnet bodies on the tissue. In any case, however, it is important that the magnet bodies 1, 2, 3 be sealed so as to be gastight. It therefore is advisable, even in the case of gastight enveloping bodies 4, to apply a protective layer of a tissue-compatible substance, since otherwise the magnet bodies 1, 2, 3 could cause harmful tissue reactions in the event of mechanical damage to the enveloping body 4. For this purpose, good results have also been obtained with the medically proven silicones.

Multi-membered permanent magnets are, of course, more adaptable to the individual lid conditions; the three-membered version described in the above embodiment may be modified in any desired manner.

Through the possibility of using high-performance permanent magnets, e.g. of $SmCo_5$, the cross-section of the eyelid permanent magnet device may be reduced by almost a factor of 4 compared to conventional magnets. Depending on the mutual assignment of the poles of the permanent magnets that are to be implanted, the inability to close or open an eyelid can be overcome by a single type of permanent magnet device.

The inventive solution can be adapted to the progressive technology of medical materials. The enveloping body could accordingly be produced from a not yet available, highly compact plastics substance without acceptance of larger dimensions. A net made for example from reinforced plastics material could enclose the individual (sealed gastight by a protective coating) magnet bodies 1, 2, 3 and, accordingly, be enveloping body and, at the same time, an ideal anchorage in the tissue.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A permanent magnet device adapted for implantation in the eyelids comprising:
   at least two magnet bodies;
   at least one spacer arranged between the magnet bodies; and
   a separate enveloping body of ductile, tissue-compatible material enclosing and clinging to the magnet bodies, said enveloping body also enclosing said at least one spacer and having at least one constriction in the radial direction located at each of said at least one spacer;
   whereby said magnet device may hold said eyelids in a desired position.

2. The permanent magnet device according to claim 1 wherein:
   the magnet bodies are rare earth-cobalt alloys.

3. The permanent magnet device according to claim 1 wherein:
   the enveloping body is tubular and closed at the ends and has a substantially rectangular cross-section.

4. The permanent magnet device according to claim 1 wherein:
   the enveloping body is tubular and closed at the ends and has a substantially elliptical cross-section.

5. The permanent magnet device according to claim 1, wherein:
   the spacer is resilient.

6. The permanent magnet device according to claim 1 wherein:
   the enveloping body consists of a metallic material selected from the group consisting of gold, silver, platinum, rhodium, ruthenium, palladium, iridium and their alloys of stainless steel.

7. The permanent magnet device according to claim 1 wherein:
   the enveloping body has end lobes.

8. The permanent magnet device according to claim 7 wherein:
   the end lobes are perforated.

9. The permanent magnet device according to claim 1 wherein:
   the enveloping body has at least one closure in the shape of a rounded projection on one part of its longitudinal side.

10. The permanent magnet device according to claim 1 including:
    a second tissue-compatible protective layer covering the magnet bodies.

11. The permanent magnet device according to claim 1 wherein:
    the enveloping body is constructed at least partly in net form.

12. The permanent magnet device according to claim 1 wherein:
    the enveloping body is covered with a net consisting of a tissue-compatible material.

13. The permanent magnet device according to claim 1 wherein:
    the enveloping body is constructed at least partly in net form and is covered with a net of tissue-compatible material.

14. The permanent magnet device according to claim 1 wherein:
    the enveloping body is approximately gastight.

* * * * *